US008025906B2

(12) United States Patent
Silva Filho et al.

(10) Patent No.: US 8,025,906 B2
(45) Date of Patent: Sep. 27, 2011

(54) **PHARMACEUTICAL COMPOSITION COMPRISING PLANT MATERIAL OR *TRICHILIA* SP. ALONE OR IN ASSOCIATION WITH OTHER PLANT EXTRACTS FOR THE REVERSION/COMBAT AND/OR PREVENTION OF VENTRICULAR FIBRILLATION**

(75) Inventors: Ney Osvaldo Silva Filho, Joinville (BR); Luc Edmond Leon Andre Raes, Joinville (BR); Carlos Eduardo De Carvalho, Joinville (BR); Irineu Tadeu Velasco, São Paulo (BR); Vera Pontieri, São Paulo (BR); Augusto Scalabrini Neto, São Paulo (BR); Celia Ivete Fernandes, São Paulo (BR)

(73) Assignee: Laboratorio Catarinense S/A, Joinville-SC (BR)

( * ) Notice: Subject to any disclaimer, the term of this patent is extended or adjusted under 35 U.S.C. 154(b) by 221 days.

(21) Appl. No.: 12/100,834

(22) Filed: Apr. 10, 2008

(65) Prior Publication Data

US 2008/0254156 A1  Oct. 16, 2008

Related U.S. Application Data

(63) Continuation of application No. 10/567,899, filed as application No. PCT/BR2004/000141 on Aug. 4, 2004, now Pat. No. 7,514,103.

(30) Foreign Application Priority Data

Aug. 8, 2003 (BR) .................................. 0302750

(51) Int. Cl.
*A61K 36/00* (2006.01)
*A61K 36/906* (2006.01)
(52) U.S. Cl. ........................ 424/725; 424/756
(58) Field of Classification Search ........................ None
See application file for complete search history.

(56) References Cited

FOREIGN PATENT DOCUMENTS

WO    WO 02/096441 A1    12/2002
WO    WO 02/096443 A1    12/2002

OTHER PUBLICATIONS

Thomas et al, Molecular mechanisms of inherited ventricular arrhythmias, Herz, (Dec. 2002) vol. 27, No. 8, pp. 712-739.*
Kirchhof et al, Molecular mechanisms of sudden cardiac death and their clinical relevance, Herzschrittmachertherapie und Elektrophysiologie, (Dec. 2003) vol. 14, No. 4, pp. 168-179.*
Bai et al, Yield of genetic screening in inherited cardiac channelopathies: how to prioritize access to genetic testing, Circulation. Arrhythmia and electrophysiology, (Feb. 2009) vol. 2, No. 1, pp. 6-15.*
Alban-Elouen et al, Role of congenital long-QT syndrome in unexplained sudden infant death: proposal for an electrocardiographic screening in relatives, European journal of pediatrics, (Jul. 2009) vol. 168, No. 7, pp. 771-777.*
Handelsman, Implantation of the automatic cardioverter-defibrillator, Health technology assessment reports, (1990) No. 10, pp. 1-9.*
Alexander, The automated external cardiac defibrillator: lifesaving device for medical emergencies, Journal of the American Dental Association (1939), (Jun. 1999) vol. 130, No. 6, pp. 837-845.*
Goodwin et al, Arrhythmia as a cause of sudden death in hypertrophic cardiomyopathy, Lancet, (1976) vol. 2, No. 7992, pp. 937-940.*
Brugada et al, A prophylactic implantable cardioverter-defibrillator? The American journal of cardiology, (Sep. 12, 1996) vol. 78, No. 5A, pp. 128-133.*
*Trichilia* species, accessed on Nov. 20, 2009, pp. 1-2.*
International Search Report for PCT/BR2004/000141 completed Oct. 21, 2004.
Pontieri et al., "The herbal drug Catuama reverts and prevents ventricular fibrillation in the isolated rabbit heart," *Journal of Electrocardiology*, 2007, pp. 534.e1-537.e8, vol. 40.
Hunt et al., "ACC/AHA 2005 Guideline Update for the Diagnosis and Management of Chronic Heart Failure in the Adult: A Report of the American College of Cardiology/American heart Association task Force on Practice Guidelines," *Circulation*, 2005, pp. e156-e235, vol. 112.

* cited by examiner

*Primary Examiner* — Qiuwen Mi
(74) *Attorney, Agent, or Firm* — Alston & Bird LLP (57) ABSTRACT

The present invention relates to the use of a plant material of the species *Trichilia* sp., alone or in association with one or more of the following plants: *Paullinia cupana* (Sapindaceae), *Croton moritibensis* (Euphorbiaceae) and *Zingiber officinale* (Zingiberaceae) in the treatment, reversion, combat and/or prevention of ventricular fibrillation. A product particularly embraced by the present invention comprises the plant material of the species *Trichilia* sp., alone or in association with extracts from other plants. The invention also refers to the use of one or more fractions of plant extract from such plant material, particularly of *Trichilia catigua* A. Juss, and of one or more subfractions of said fractions in the treatment, combat, prevention and/or reversion of ventricular fibrillation.

13 Claims, 11 Drawing Sheets

PHARMACEUTICAL COMPOSITION COMPRISING PLANT MATERIAL OR *TRICHILIA* SP. ALONE OR IN ASSOCIATION WITH OTHER PLANT EXTRACTS FOR THE REVERSION/COMBAT AND/OR PREVENTION OF VENTRICULAR FIBRILLATION

CROSS-REFERENCE TO RELATED APPLICATIONS

This application is a continuation of U.S. application Ser. No. 10/567,899, filed Aug. 10, 2006 now issued as U.S. Pat. No. 7,514,103, which is the U.S. National Stage of International Application No. PCT/BR2004/000141, filed Aug. 4, 2004, which claims the benefit of Brazilian Patent Application No. PI0302750-3, filed Aug. 8, 2003; all of which are hereby incorporated herein in their entirety by reference.

FIELD OF THE INVENTION

The present invention relates to the use of a plant material of the species *Trichilia* sp., alone or in association with extracts from one or more of the following plants: *Paullinia cupana* (Sapindaceae), *Croton moritibensis* (Euphorbiaceae) and *Zingiber officinale* (Zingiberaceae).

The present invention relates, in particular, to the use of one or more fractions of a plant extract from plant material of *Trichilia catigua* A. Juss., or one or more subfractions of said fractions in the reversion of ventricular fibrillation and/or prevention of ventricular fibrillation.

BACKGROUND OF THE INVENTION

Medicinal plants known as catuaba (*Trichilia* sp.) have recognized uses due to their stimulating activities for the nervous system, specially for sexual incapacity of the male genital organs, and as a tonic in the treatment of physical and mental fatigue. For example, *Trichilia catigua* A. Juss is greatly used for such purpose.

*Trichilia catigua* A. Juss is a Brazilian medicinal plant, abundantly growing in the north and northeast of the country. Although this plant has been used for centuries by the native population, there are few scientific studies for demonstrating the pharmaceutical properties thereof or their phytochemical composition.

Already known are, e.g., phytotherapeutic formulations prepared from extracts of catuaba plants (*Trichilia* sp.), which can be used alone or in combination with other medicinal plant extracts, such as guarana. A number of alternative formulations containing extracts of other species of catuaba are already well-known from the state-of-the-art, all of them being related to the tonic and stimulating effect of this group of plants.

There already exist in the art phytotherapeutical products comprising a combination of extracts from plants of the *Trichilia* sp. species, particularly *Trichilia catigua* (Meliaceae), *Paullinia cupana* (Sapindaceae), *Croton moritibensis* (Euphorbiaceae) and *Zingiber officinale* (Zingiberaceae), for example.

A commercially available product, related to that tonic and stimulating effect, and comprising extracts from the above-mentioned plants in combination with suitable carriers is Catuama®, Catuama®, in particular, is a phytotherapeutic drug widely used in Brazil. Its composition consists of 4 extracts from medicinal plants including: catuaba (*Trichilia catigua* A. Juss, Meliaceae—plant), guarana (*Paullinia cupana* Kunth, Sapinadaceae—seeds), muirapuama (*Croton moritibensis* Baill., Euphorbiaceae—root) and ginger (*Zingiber officinale* Roscoe, Zingiberaceae—rhizome).

On the other hand, it is known that ventricular fibrillation is the major cause of sudden death, being present at 70% of the cases of cardiac standstill, specially in patients suffering from coronary cardiopathy. Its electrophysiological mechanism involves a great disorganization of cardiac electrical activity, with changes in the conduction of the stimulus and ventricular repolarization leading to the development of multiple reentrant circuits, the so-called fibrillation "rotors". It often occurs as the ultimate event of a cardiopathy.

The survival rate for this arrhythmia is still too low, less than 5%. Even for those individuals who achieve reversion at sinus rhythm, hospital discharge rate is disappointing. Thus, there is a great interest in finding and standardizing measures which increase survival in such a critical condition.

So far, the only available treatment for this arrhythmia is the electrical defibrillation. According to American Heart Association recommendations, electrical defibrillation should always be tried as a first treatment, and may subsequently be associated to the use of pharmaceuticals. The major difficulty with this therapy resides in two facts: first, the defibrillator may only be used by well-trained people, even in the case of semi-automatic models, and its cost is very high; second, the defibrillation time is critical, it being known that at every minute the chances of an effective reversion is reduced by 10%. Thus, a simple measure, which could be quickly used by individuals with no specific training, would be greatly useful.

SUMMARY OF THE INVENTION

The present invention refers to the use of plant material of the species *Trichilia* sp., alone (as the single plant material or its extract) or in association with extracts from one or more of the following plants: *Paullinia cupana* (Sapindaceae), *Croton moritibensis* (Euphorbiaceae) and *Zingiber officinale* (Zingiberaceae), in the reversion/combat and/or prevention of ventricular fibrillation.

In another aspect, this invention refers to pharmaceutical compositions comprising said plant material for the reversion/combat and/or prevention of ventricular fibrillation.

In yet another aspect, this invention refers to a method for the reversion/combat and/or prevention of ventricular fibrillation using said plant material alone or in association with extracts from other appropriate plants.

In still another embodiment, the invention refers to the use of a product comprising plant material of the species *Trichilia* sp., alone or in association with extracts from one or more of the following plants: *Paullinia cupana* (Sapindaceae), *Croton moritibensis* (Euphorbiaceae) and *Zingiber officinale* (Zingiberaceae), for preparing a pharmaceutical composition for the reversion/combat and/or prevention of ventricular fibrillation.

More particularly, the present invention relates to pharmaceutical compositions comprising *Trichilia catigua* A. Juss (as an extract or in combination with other plants mentioned herein) and the use of one or more fractions of plant extract from the plant material of *Trichilia catigua* A. Juss, or of one or more subfractions of said fractions in the reversion of ventricular fibrillation and/or protection against ventricular fibrillation.

In another aspect, the invention particularly relates to the use of said fractions or subfractions of *Trichilia catigua* A.

Juss for manufacturing a pharmaceutical composition or form for use in the reversion and/or protection against ventricular fibrillation.

In still another aspect, the invention refers to a method for reverting and/or protecting against ventricular fibrillation particularly using said fractions and subfractions of the species *Trichilia* sp.

In another embodiment, the invention refers to a method of extracting plant material, particularly from *Trichilia catigua* A. Juss for obtaining the respective plant extract of *Trichilia catigua* A. Juss.

And finally, the invention relates to a method of fractionation of said plant extract for obtaining said main fractions and subfractions.

DETAILED DESCRIPTION OF THE INVENTION

After extensive studies, the inventors have found that plant material of the species *Trichilia* sp., whether or not in association with extracts from one or more of the following plants: *Paullinia cupana* (Sapindaceae), *Croton moritibensis* (Euphorbiaceae) and *Zingiber officinale* (Zingiberaceae), has surprising effects on the reversion/combat and/or prevention of ventricular fibrillation.

More particularly, they found out that one or more fractions of the plant extract from plant material of *Trichilia catigua* A. Juss, as well as one or more subfractions of said fractions, have surprising effects on the reversion and/or protection against ventricular fibrillation.

During the studies carried out with plant material of the species *Trichilia* sp., alone or in association with extracts from one or more of the previous cited plants, in isolated heart for examining its action on myocardial contractility, some both rat and rabbit hearts showed ventricular fibrillation after ligature of coronary artery, and the use of plant material of the species *Trichilia* sp. alone or in such association within the bath the organs were in, permanently reverted fibrillation in several hearts.

More particularly, it was observed that, in such situation, the use of extract from plant material of *Trichilia catigua* A. Juss., and later a primary fraction of said extract and also one or more subfractions of said fraction, in the bath the organs were in, permanently reverted fibrillation, and in several hearts, e protected those hearts against new induced fibrillation.

Ventricular fibrillation is a pathology characterized by an uncoordinated and potentially fatal series of very quickly and ineffectively ventricular contractions produced by multiple chaotic electrical impulses.

From the electrical point of view, ventricular fibrillation is similar to atrial fibrillation, showing, however, a much more severe prognosis. In ventricular fibrillation, ventricles shake and do not coordinately contract. As blood is not pumped to the heart, ventricular fibrillation represents a type of cardiac standstill and, unless promptly treated, is fatal.

The causes of ventricular fibrillation are the same as those of cardiac standstill. The most common is inadequate blood flow to the myocardium due to the coronary artery disease or a myocardial infarction. Other causes include shock at very low blood levels of potassium (hypokalemia).

Ventricular fibrillation causes loss of consciousness in just a few seconds. If not treated, the individual usually has convulsions crisis and irreversible brain injury after about five minutes, because there is no more transport of oxygen to the brain. Thereafter comes death.

Several products comprising variable concentrations of extracts of the above plants are commercially available. The use thereof, so far recommended in the art, is related to the treatment of physical and mental fatigues.

Studies and researches now carried out by the present inventors show their efficacy in combating/reverting and/or preventing ventricular fibrillation related to products based on plant material of the species *Trichilia* sp. alone or in association with extracts from one or more of the previous plants. Said studies show, in particular, their efficacy in reverting and protecting against ventricular fibrillation particularly related to extracts based on plant material of *Trichilia catigua* A. Juss, with one or more fractions of said extract and one or more subfractions of said fractions, as confirmed by the data and tests disclosed herein.

The concentration of the extract of each plant of *Trichilia* sp., *Paullinia cupana, Croton moritibensis* and *Zingiber officinale*, in the product or pharmaceutical composition of the present invention is as follows:

| Liquid formulation: | | |
| --- | --- | --- |
| | % (m/v) | |
| Component | Generic | Preferred |
| Extract of *Trichilia* sp. (specially *Trichilia catigua* A. Juss) | 0.50 to 10.0 | 0.50 to 5.00 |
| Extract of *Paullinia cupana* | 0.10 to 7.50 | 0.1 to 5.00 |
| Extract of *Croton moritibensis* | 0.01 to 5.50 | 0.01 to 5.0 |
| Extract of *Zingiber officinale* | 0.10 to 2.00 | 0.1 to 0.40 |
| Suitable excipient | 79.50 to 99.29 | 84.60 to 99.24 |

| Solid formulation: | | |
| --- | --- | --- |
| | % (m/m) | |
| Component | Generic | Preferred |
| Extract of *Trichilia* sp. (specially *Trichilia catigua* A. Juss) | 5 to 100 | 30 to 50 |
| Extract of *Paullinia cupana* | 2 to 30 | 10 to 21 |
| Extract of *Croton moritibensis* | 0.2 to 15.0 | 5 to 12 |
| Extract of *Zingiber officinale* | 0.5 to 3.0 | 0.5 to 1.5 |
| Suitable excipient | 2 to 92.30 | 15.5 to 54.5 |

In its dry and excipient-free form, the product or pharmaceutical composition of the present invention comprises:

| Formulation | | |
| --- | --- | --- |
| | % (m/m) | |
| Component | Generic | Preferred |
| Extract of *Trichilia* sp. (specially *Trichilia catigua* A. Juss) | 17 to 100 | 22 to 34 |
| Extract of *Paullinia cupana* | 24 to 57 | 32 to 48 |
| Extract of *Croton moritibensis* | 17 to 40 | 22 to 34 |
| Extract of *Zingiber officinale* | 2 to 5 | 2.5 to 4.0 |

The product may comprise usual excipients for formulation such as preservatives, colorants, carriers, etc. Suitable excipients are well known by those skilled in the art and do not constitute limiting aspects of the invention.

By "plant material" or "extract of plant material" it is meant extracts from the respective plants, for example, from *Trichilia* sp., particularly *T. catigua* A. Juss, particularly from hulls, stems, branches, leaves and other parts or fragments of plants susceptible of producing appropriate extracts therefrom.

For the purposes of the present invention, all plants of the genus *Trichilia* were found to be useful, such as, e.g., *T. catigua* A. Juss., *T. emarginata* (Turcz.) C. DC., *T. clausseni* C. DC., *T. casaretti* C. DC., *T. pallida* Swartz. and *T. elegans* A. Juss. According to a preferred embodiment of the present invention, it was found that, among the genera comprised of species *Trichilia, Trichilia* sp. and *T. catigua* A. Juss. are more particularly suitable for the intended purposes. Additionally, the materials extracted from species *Trichilia* sp. and *T. catigua* A. Juss. can be fragments of the whole plant, hulls, stems, branches, leaves and other parts which are advantageously used as extract, and more preferably they can be formulated with pharmaceutically acceptable inert carriers. Formulations of *Trichilia* sp., in particular *T. catigua* A. Juss., useful for the present invention can be administered, but not limited to, e.g., orally in the form of tablets, coated tablets, hard and soft gelatin capsules, solutions, emulsions and suspensions; or rectally, in the form of suppositories. Suitable carriers include, but are not limited to, lactose, starch or derivatives thereof, talc, stearic acid or salts thereof in the case of solid formulations for oral administration. Suitable carriers for soft gelatin capsules include vegetable oils, waxes, fats, semi-solid and liquid polyols. Solutions may be prepared comprising selected carriers such as water, polyols and carbohydrates. In the case of suppositories, suitable carriers comprise natural or hardened oils, waxes, fats and polyols.

In addition to the carriers, the formulations of the product or pharmaceutical composition according to the present invention may contain preservative agents, solubilizing agents, stabilizers, wetting agents, emulsifiers, sweeteners, dye agents, flavoring agents, tonicity adjustment substances, buffers, coating agents or anti-oxidants.

However, an effective dosage for administration to humans was found to be in the range corresponding to from 10 mg to 0.5 g of product or pharmaceutical composition of the present invention.

In the case of pharmaceutical formulations containing plant material of the species *Trichilia* sp., alone or in association with extracts from the previously cited plants, the intended effects can be effectively achieved using from 0.2 to 100% by weight of said extract, based on the total formulation.

The process for preparing the extracts of the present invention usually comprises grinding the hull of *Trichilia* followed by extracting in a solvent, e.g. alcohol, and water. Extraction is usually carried out in temperatures of about 60° C. for an appropriate period of time to obtain a suitable extraction. More than one extraction cycle can be carried out and the respective extracts from each cycle may be combined to obtain the intended final extract product. Intermediate extracts from each cycle are concentrated under pressure and each is later combined for producing the final extract at the desired concentration. The following illustrates the preparation of extracts from *Trichilia catigua* A. Juss using it hull thereof as starting material. It is further illustrated how to obtain fractions and subfractions thereof.

Preparation of Plant Material

The process for manufacturing plant extract from *Trichilia catigua* A. Juss begins by grinding the hull of the plant. Thereafter a step of first extraction follows using a ratio of alcohol and water (5:1) at a temperature of 60° C. for 4 hours, exhausting the plant with compressed air. Then a first concentration is made with vapor pressure at a temperature of 80° C. In the second and third extractions, extraction of the residue from the first extraction takes place, using 20% of the ratio alcohol and water (5:1) at a temperature of 60° C. for 3 hours, wherein 80% of the extracting mixture is recovered. This procedure ends with the plant exhaustion with compressed air. Thereafter second and third concentrations with vapor pressure at a temperature of 80° C. are performed. Afterwards, all three extracts are mixed together and the final concentration is carried out up to the desired marker contents.

Preparation of Fractions and Subfractions

Figure 11:
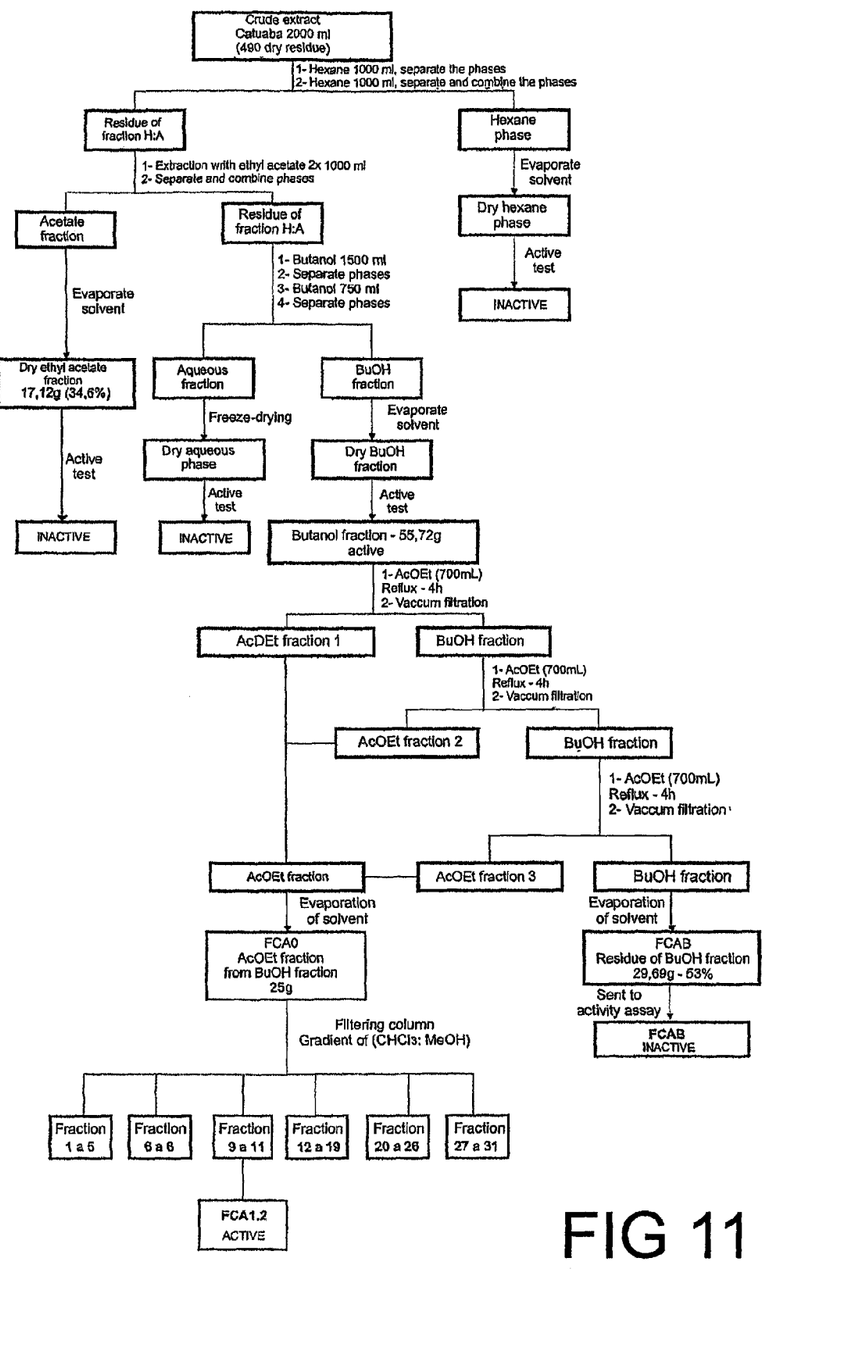
FIG. 11 illustrates a possible flowchart of how to obtain fraction and subfractions of the extract from *Trichilia catigua* A. Juss.

The extracting process begins with the preparation of a crude extract (H:A) of *Trichilia catigua* A. Juss with formation of a dry residue, as described above. Perform extraction twice from the crude extract with hexane. Separate the two formed phases (hexane phase and fraction residue H:A). HEXANE PHASE: evaporate solvent to obtain a dry hexane phase; FRACTION RESIDUE H:A: carry out extraction twice with ethyl acetate. Separate and combine the phases (acetate fraction and fraction residue H:A); ACETATE FRACTION: evaporate solvent obtaining a dry ethyl acetate fraction; FRACTION RESIDUE H:A: conduct extraction twice with butanol and separate the two fractions which were formed (aqueous fraction and butanol fraction); AQUEOUS PHASE: freeze-dry to obtain a dry aqueous fraction; BUTANOL FRACTION: evaporate solvent to obtain a dry butanol fraction; SUBFRACTIONS OF THE BUTANOL FRACTION: butanol phase is dry column (8 columns) fractionated. Each column shows 60 cm, 100 g silica, a ratio of $CHCl_3$:MeOH (60:40) to elute, and four fractions of 10 cm each are then obtained (precipitate; fractions 1 e 2; fractions 3 e 4; residue). FIG. 11 shows a possible flowchart of how to obtain fraction and subfractions.

This invention will now be described specifically regarding plant material of species *Trichilia* sp. Alone or in association with extracts from the other cited plants, also the applicant's, already commercial available in Brazil for treating several other long-term diseases. The advantage of this product is associated to the absence of any side or undesirable effects reported, even when the product is used for extended periods of time.

More particularly, the invention will be more specifically described regarding plant material of *Trichilia catigua* A. Juss., primary fractions of this plant extract and subfractions of such fractions.

Altogether, the results discussed clearly show that plant material of species *Trichilia* sp., particularly *Trichilia catigua* A. Juss., (alone or in association with the other plant extracts previously mentioned) now described in the present invention exhibits efficacy in reverting and/or preventing ventricular fibrillation.

The present invention refers to the effects of plant material of species *Trichilia* sp. alone or in association with the other plant extracts previously mentioned, more particularly *Trichilia catigua* A. Juss., on pathologies involving changes in the cardiovascular system, essentially in combating, preventing and/or reverting ventricular fibrillation. Substances which may combat/revert ventricular fibrillation, such as plant material of species *Trichilia* sp. alone or in such association, are of particular importance when administrated acutely, since ventricular fibrillation must be treated as an emergency and the only procedure now available for reverting ventricular fibrillation is the electrical shock on the heart.

Still more important is the fact that, once reverted, relapsing of ventricular fibrillation does not occur in the presence of plant material of species *Trichilia* sp. alone or in the above mentioned association, something not occurring with the procedure currently available with electrical shock on the heart.

Figure 1:
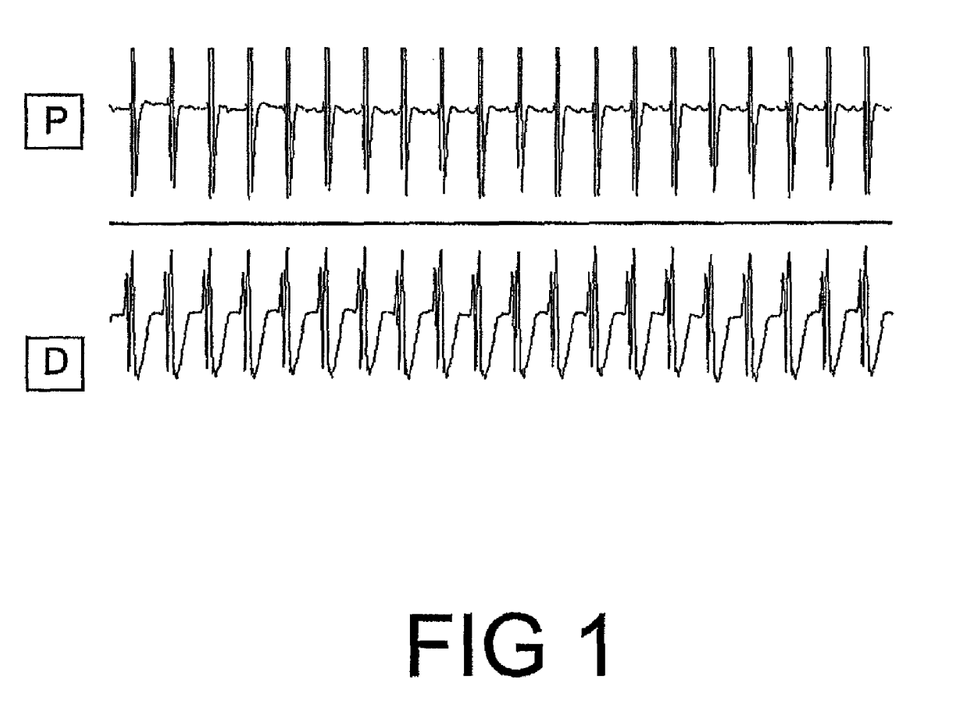
FIG. 1 shows plots of electrograms P and D of an isolated rabbit heart.
Figure 2:
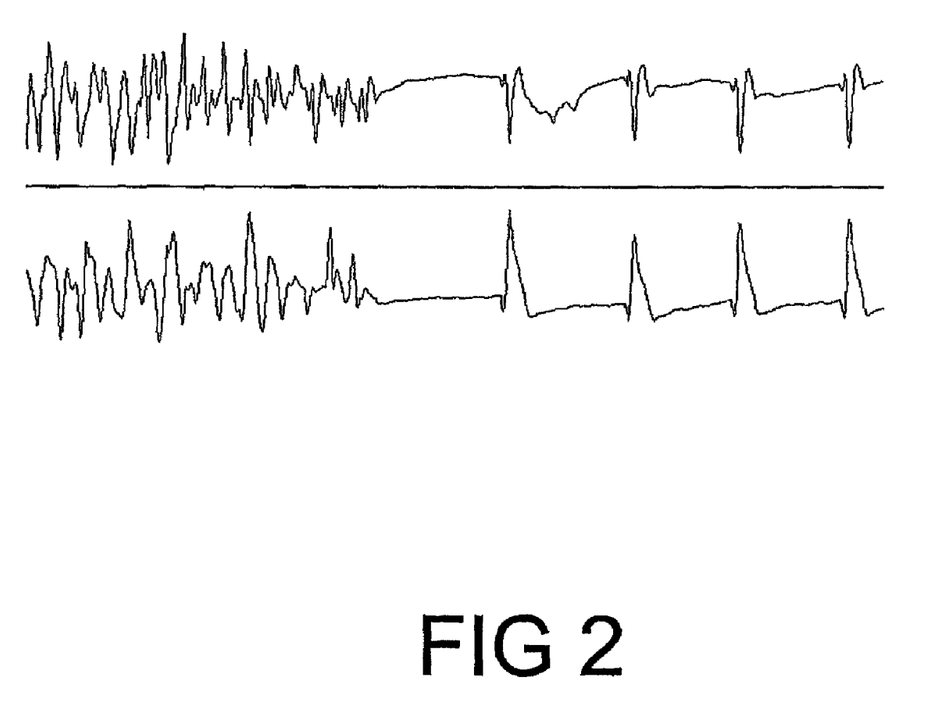
FIG. 2 shows reversion of ventricular fibrillation of the isolated rabbit heart by endocardial stimulus with plant material of species *Trichilia* sp. alone or in the above cited association.
Figure 3:
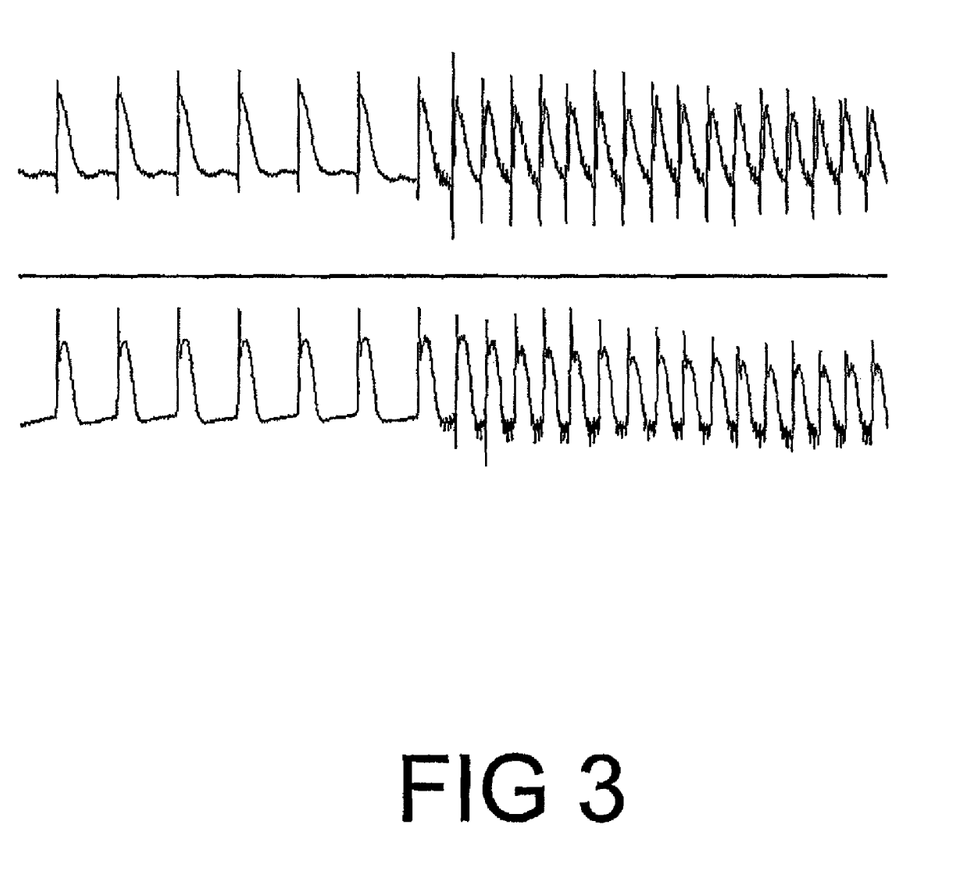
FIG. 3 shows an attempt of reinduction of ventricular fibrillation in the isolated rabbit heart, in the presence of plant material of species *Trichilia* sp. alone or in the above cited association. A new ventricular fibrillation with electrical stimulus generated in the present of plant material of species *Trichilia* sp. whether or not in association is not obtained.
Figure 4:
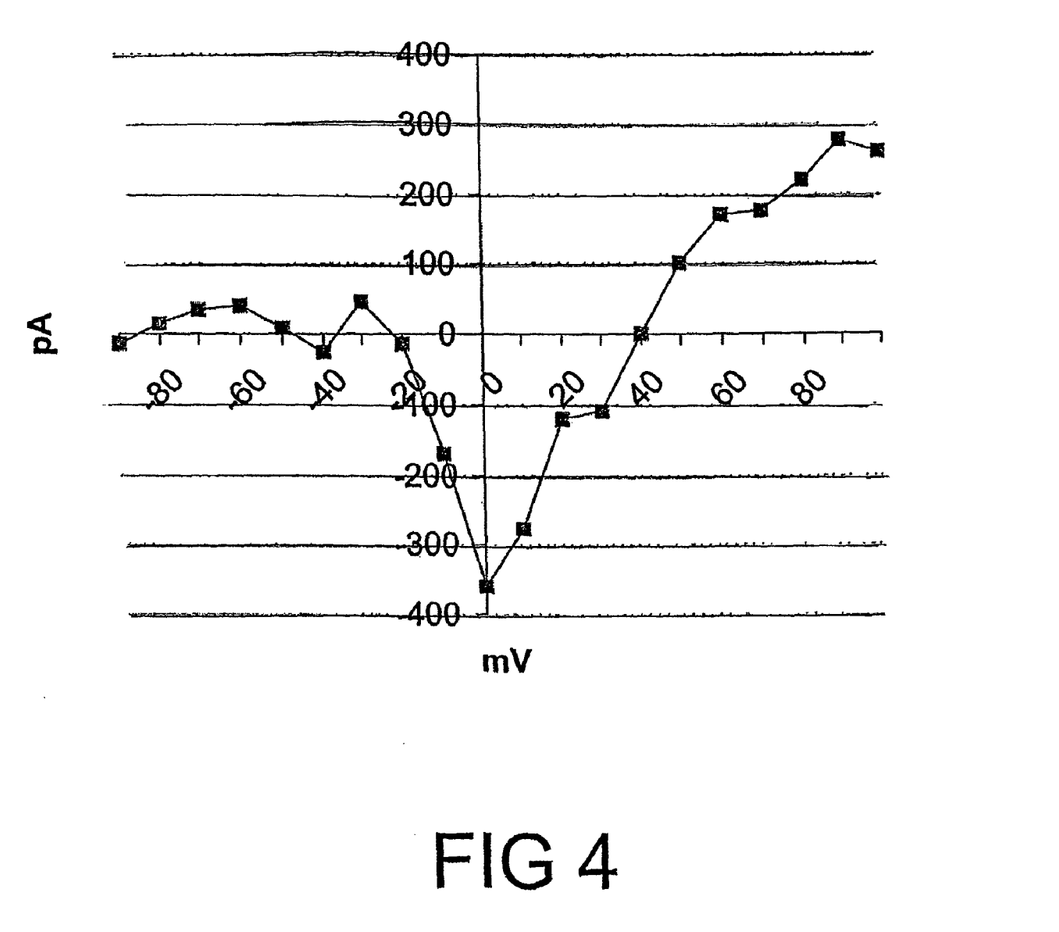
FIG. 4 shows the results of an experiment of patch-clamp control in isolated cell-isolated neuron. It shows that the sodium channels remain open.
Figure 5:
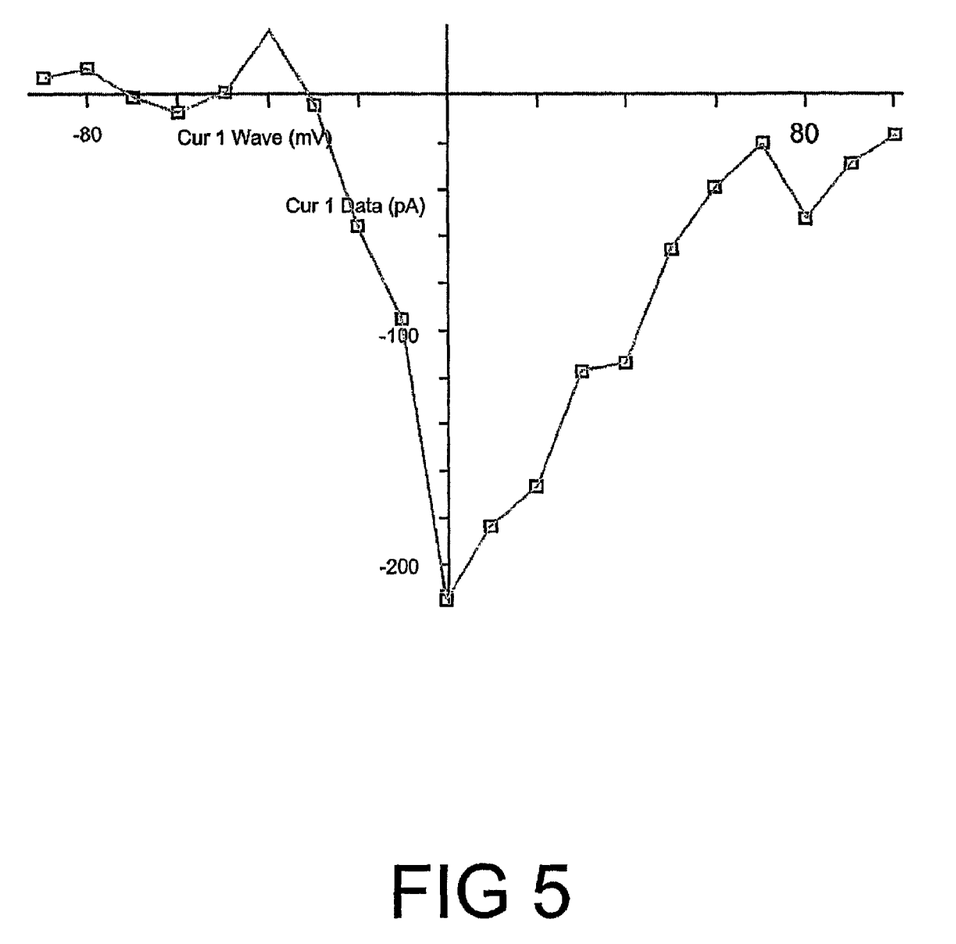
FIG. 5 shows the results of an experiment of patch-clamp control with the plant material of species *Trichilia* sp. whether or not in association (200 µg/ml product or pharmaceutical composition of the present invention), time (T)=0.
Figure 6:
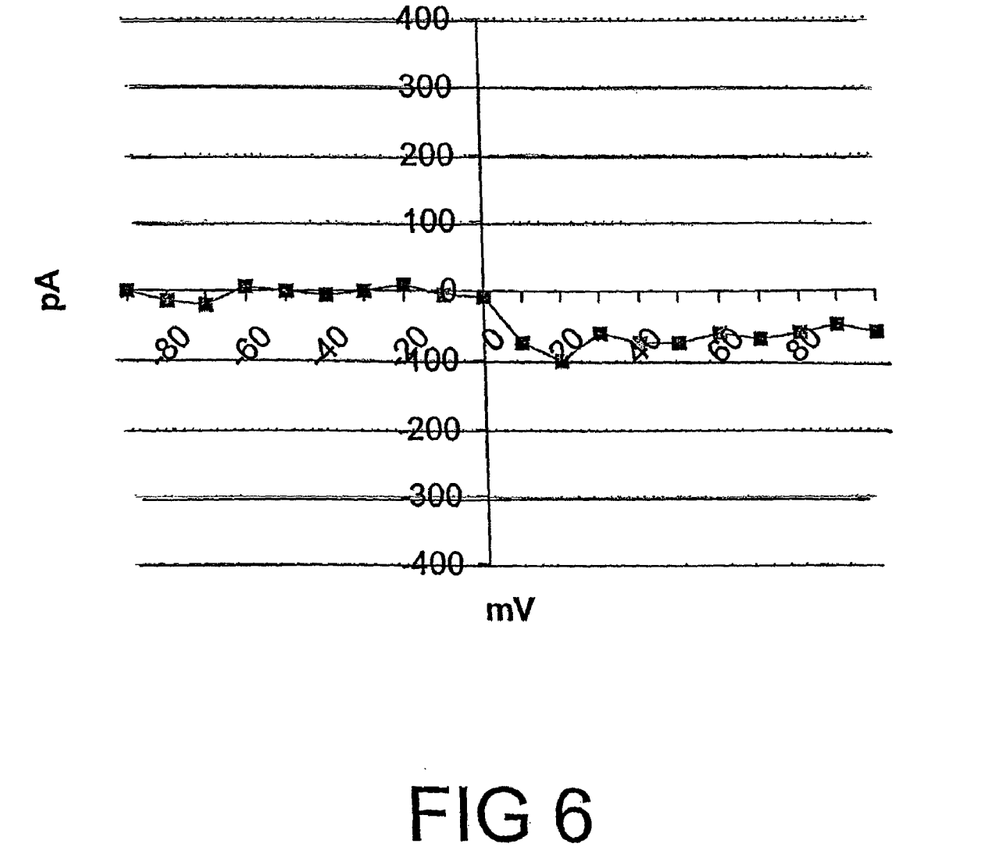
FIG. 6 shows the results of an experiment of patch-clamp control with the plant material of species *Trichilia* sp. whether or not in association (200 µg/ml product or pharmaceutical composition of the present invention), time (T)=2 minutes.
Figure 7:
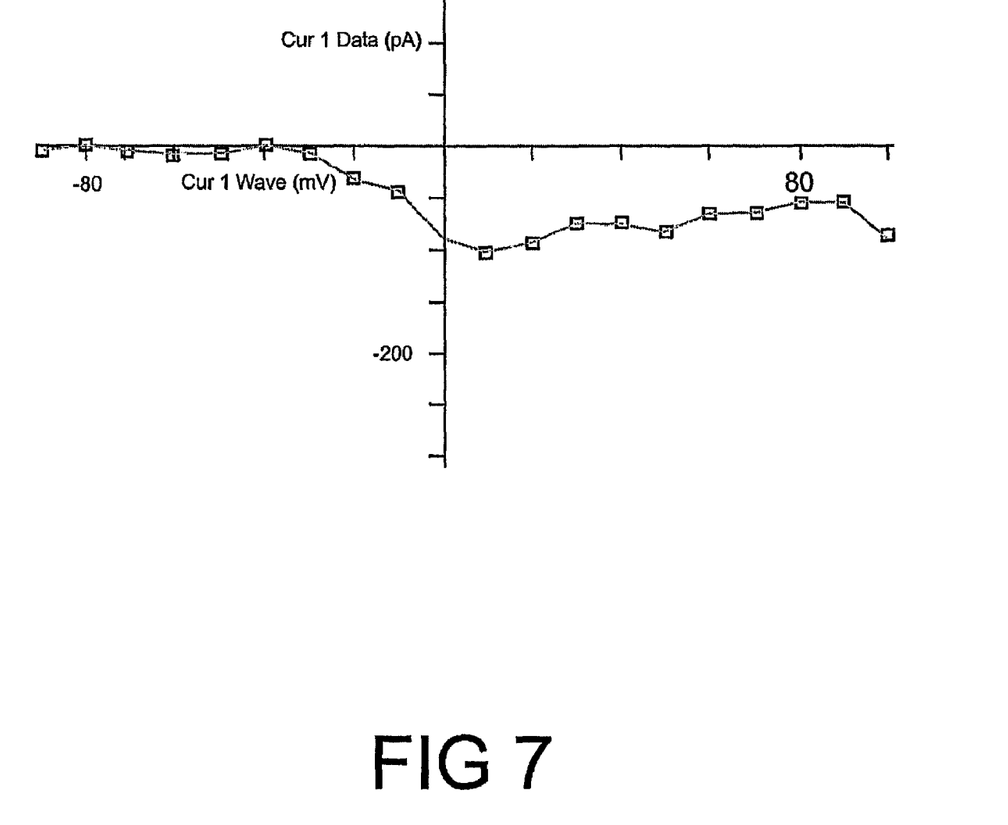
FIG. 7 shows the results of an experiment of patch-clamp with the plant material of species *Trichilia* sp. alone or in the above cited association (200 µg/ml product or pharmaceutical composition of the present invention), time (T)=5 minutes.
Figure 8:
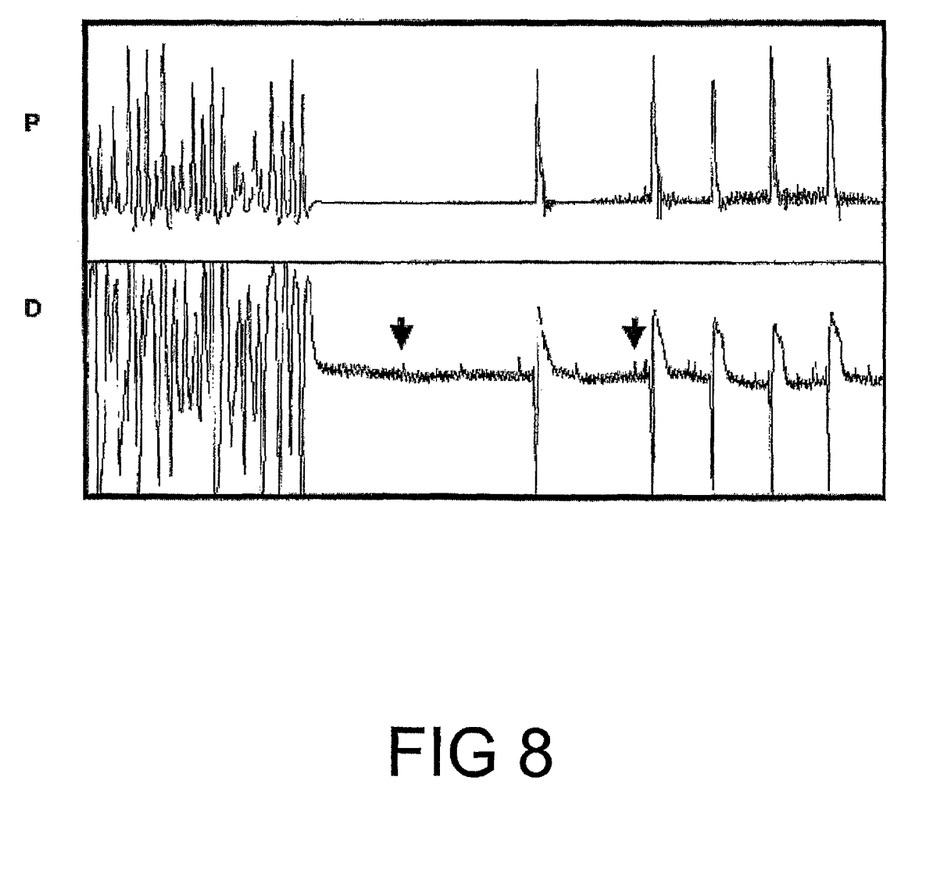
FIG. 8 shows reversion of ventricular fibrillation sustained by a typical experiment with the product containing *Trichilia catigua* A. Juss (Catuama group). Note the reversion of ventricular fibrillation immediately after addition of catuaba to perfusate, with subsequent command of supraventricular rhythm (probably sinus). P=electrogram recording obtained from the proximal pair of electrodes; D=electrogram recording obtained from the distal pair of electrodes; arrow=plots the atrial electrogram recording.
Figure 9:
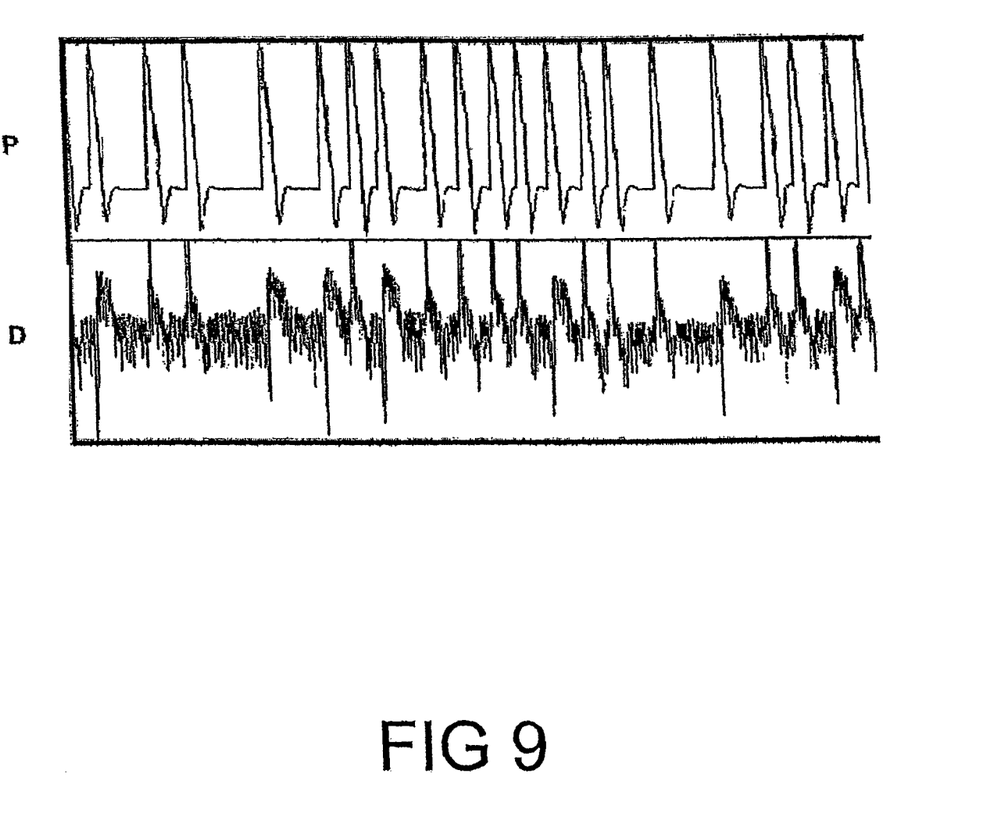
FIG. 9—An attempt of reinduction of ventricular fibrillation in a typical experiment with the product containing *Trichilia catigua* A. Juss (Catuama group). Note that in spite of electrical stimulation a new ventricular fibrillation does not occur. P=electrogram recording obtained from the proximal pair of electrodes; D=electrogram recording obtained from the distal pair of electrodes.
Figure 10:
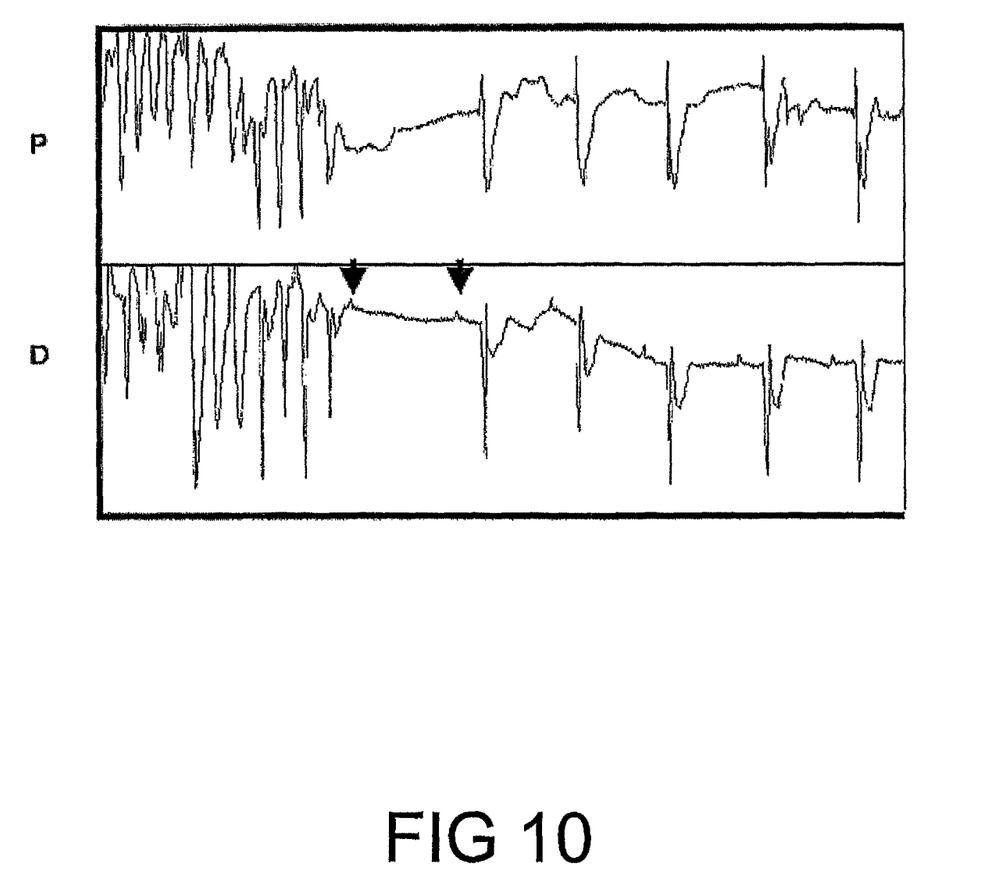
FIG. 10—Reversion of ventricular fibrillation sustained in a typical experiment with catuaba group (extract from *Trichilia catigua* A. Juss). Note the reversion of ventricular fibrillation immediately after addition of catuaba to perfusate, with subsequent command of supraventricular rhythm (probably sinus). P=electrogram recording obtained from the proximal pair of electrodes; D=electrogram recording obtained from the distal pair of electrodes; arrow=plots the atrial electrogram recording.

The results disclosed in FIGS. 5, 6 and 7 show inhibition of the sodium channel by plant material of species *Trichilia* sp. whether or not in association (200 µg/ml product or pharmaceutical composition of the present invention, at times (T) 0, 2 and 5 minutes, keeping them closed).

To demonstrate the effect of plant material of species *Trichilia* sp. alone or in the above cited association on ventricular fibrillation in isolated heart, the following protocol was carried out.

To carry out those experiments, white New Zealand rabbits were killed by cervical displacement. The thorax was quickly opened, the heart removed and suspended in a traditional Langendorff preparation. A perfusion with standard Krebs solution, saturated with carbogen, was set. After a 10 minutes stabilization period, the system was closed in 150 ml of Krebs solution. Pairs of electrodes were then sutured on the epicardial surface of the left ventricle (VE); one pair at top of VE (proximal=P) and the other at the bifurcation of arteries DA and DI (distal=D). Recordings were obtained of bipolar electrograms P and D at frequency cutoff between 50 and 500 Hz. The time for intraventricular conduction of stimulus (P-D) was measured. A bipolar electrode was placed on the endocardium to allow electrical stimulus and production of ventricular fibrillation maintained for 20 minutes. The stimulation continued for 5 minutes at a 10 V voltage, 3 min duration and 50 Hz frequency.

After achieving a stable fibrillation, control group was observed for 20 minutes; the product or pharmaceutical composition of the present invention was administered to the test group (20 µg/ml) after 20 minutes of ventricular fibrillation, while the group SHAM received Tween 80 (20 µg/ml) after 20 minutes of ventricular fibrillation.

After reversion in sinus rhythm, a new stimulation was carried out attempting a new ventricular fibrillation.

In a preferred embodiment in order to verify the effect of plant material of *Trichilia catigua* A. Juss. on ventricular fibrillation in isolated heart, the following protocol was carried out.

To carry out those experiments, twenty-seven white New Zealand rabbits both male and female, weighing from 2.5 to 3.5 kg, were heparinized with 100 Ul/kg of intravenous heparin and killed by cervical displacement.

The thorax was quickly opened through a median incision and the sternum opened to both sides for complete exposure of the thorax inside. The pericardium was removed and the ascendant part of isolated aorta and repaired with a cotton thread 3-0. A metal cannula was then inserted into and fixed on the aorta proximal portion and back perfusion of Krebs-Henseleit solution oxygenated and heated at 37° C. was started through that cannula with a constant rate of 13 ml/minute kept by a continuous infusion pump Harvard Apparatus model RS232. The cannula's tip was positioned very close to the valva aortae to allow suitable coronary perfusion.

The heart was then removed and suspended through the cannula in a traditional Langendorff preparation. The composition of Krebs Hanseleit solution was: 115 mM NaCl; 5.4 mM KCl; 1.25 mM $CaCl_2$; 25 mM $NaHCO_3$; 1.2 mM $MgSO_4$; 1.15 mM $NaH_2PO_4$; and 11 nM glucose. A drain was placed within the left ventricle (VE) to avoid liquid accumulation.

Two pairs of electrodes (Monicron 2-O) were sutured on the surface of the left ventricle (VE); one at the top, called proximal (P) and the other at the bifurcation of the prior descendent coronary artery with the first diagonal, called distal (D). Electrograms obtained from electrodes P and D were acquired through a acquisition system ECG 100B from Biopac Systems Inc. and continuously registered throughout the experiment by Acknowledge version 3.5.5, a software from Biopac Systems Inc. as well, at frequency cutoff between 50 and 500 Hz. Heart frequency was determined by measurement of the interval between two consecutive electrograms and converted into beats per minute (bpm). The values taken into consideration were the average of 5 consecutive measurements.

For stabilization, the preparation was initially kept with open perfusion of Krebs solution, which perfused the coronaries and was discarded. After stabilizing for 20 minutes, the system was closed and the perfusate recycled with 150 ml of solution.

A bipolar electrode was positioned and fixed on the endocardium surface of the right ventricle (VO) through an incision across the arteria pulmonalis. Through this electrode a continuous electrical stimulus was caused at the endocardium of VD for 5 minutes in order to trigger ventricular fibrillation. The stimulus was applied by means of a customized programmable stimulator. The electrical stimulus was at a 50 Hz frequency; 2 min duration; 10 V voltages; and 10 mA current.

After ventricular fibrillation kept for 20 minutes, extract of *Trichilia catigua* A. Juss was added as a composition form (applicant's product Catuama®) or as an extract of Catuaba to the perfusate in order to test for the anti-fibrillation effect and in the cases where reversion occurred a new attempt of inducing ventricular fibrillation after 5 minutes was made to determine the protecting effect.

The following tables disclose the findings in the hearts of the experimental groups. The results refer to the use of compositions comprising the product of *Trichilia catigua* A. Juss extract in association with other extracts (Catuama group—Table 1) as well as the *Trichilia catigua* A. Juss extract itself (Catuaba group—Table 2), thus showing the positive effects of *Trichilia catigua* A. Juss extract as well as those of the association thereof with the further plant extracts specified herein.

TABLE 1

|  | Time VF (min) | FC pre (bpm) | FC post (bpm) | Time (min) | Pause (min) | Reinduction |
|---|---|---|---|---|---|---|
| Catuama group | 20.0 | 110.0 | 68.0 | 240.0 | 1000.0 | NF |
|  | 20.0 | 65.0 | 105.0 | 90.0 | 890.0 | NF |
|  | 20.0 | 115.0 | 84.0 | 270.0 | 930.0 | NF |
|  | 20.0 | 130.0 | 134.0 | 100.0 | 615.0 | NF |
|  | 20.0 | 112.0 | 115.0 | 240.0 | 530.0 | NF |
|  | 20.0 | 122.0 | 139.0 | 60.0 | 720.0 | NF |
| Ave. S.E. | 20.0 | 109.0 | 107.5 | 166.7 | 780.8 |  |
|  | 0.0 | 22.8 | 27.8 | 92.9 | 187.8 |  |

Table 1—Results obtained upon administration of the product containing *Trichilia catigua* A. Juss (Catuama group mentioned above) to the perfusate of isolated rabbit hearts under ventricular fibrillation. Time VF=time of heart fibrillation; FC pre=heart frequency in bpm before induction of ventricular fibrillation; FC post=heart frequency in bpm after reversion of ventricular fibrillation; Time=lapse of time, in milliseconds, between addition of the product comprising *Trichilia catigua* A. Juss to the perfusate and reversion of arrhythmia; Pause=lapse of time, in milliseconds, between reversion of VF and the beginning of sinus rhythm; NT=not tested; NF=impossible to reinduce VF after reversion; S.E.=standard error.

TABLE 2

|  | Time VF (min) | FC pre (bpm) | FC post (bpm) | Time (min) | Pause (min) | Reinduction |
|---|---|---|---|---|---|---|
| Catuaba group | 20.0 | 146.0 | 108.0 | 210.0 | 805.0 | NF |
|  | 20.0 | 160.0 | 130.0 | 80.0 | 435.0 | NF |
|  | 20.0 | 126.0 | 136.0 | 70.0 | 620.0 | NF |
|  | 20.0 | 105.0 | 105.0 | 180.0 | 500.0 | NF |
|  | 20.0 | 114.0 | 203.0 | 180.0 | 452.0 | NF |
|  | 20.0 | 105.0 | 203.0 | 270.0 | 520.0 | NF |
| Ave. S.E. | 20.0 | 126.0 | 147.5 | 165.0 | 555.3 |  |
|  | 0.0 | 22.7 | 44.6 | 77.1 | 138.6 |  |

Table 2—Results obtained upon administration of catuaba to the perfusate of isolated rabbit hearts under ventricular fibrillation. Time VF=time of heart fibrillation; FC pre=heart frequency in bpm before induction of ventricular fibrillation; FC post=heart frequency in bpm after reversion of ventricular fibrillation; Time=lapse of time, in milliseconds, between addition of the substance to the perfusate and reversion of arrhythmia; Pause=lapse of time, in milliseconds, between reversion of VF and the beginning of sinus rhythm; NT=not tested; NF=impossible to reinduce VF after reversion; S.E.=standard error.

The product containing *Trichilia catigua* A. Juss (Catuama group) or the extract itself from the plant (Catuaba group) reverted sustained ventricular fibrillation induced in isolated rabbit heart in traditional Langendorff preparation. Additionally, it prevented reinduction of ventricular fibrillation in those hearts. The mechanisms though which *Trichilia catigua* A. Juss exerts such effect is not fully understood.

It is known that ventricular fibrillation depends on multiple reentrant circuits, or "rotors", to maintain it. The presence of multiple reentrant circuits requires the tissue which it lies on to be long enough, and the stimulus conduction and ventricular repolarization to have critical speed and duration. Specially, the ventricular repolarization must compulsorily be shortened or asynchronous in order to maintain a compatible wavelength.

Several drugs and substances change the ventricular repolarization, leading to a situation of enlargement of interval QT and as a result to malignant ventricular arrhythmia. Thus, changes in ventricular repolarization seem to play a critical role in the development of such arrhythmia conditions, and possibly in the reversion thereof.

So far there are no studies showing the effects of *Trichilia catigua* A. Juss. on the electrophysiological parameters of the heart. Thus, providing a mechanism for its anti-fibrillation effect becomes difficult. Similarly to other substances of anti-arrhythmic effects, it can be contemplated that an effect on ventricular repolarization plays an important role on such action.

This, however, is only a first observation. Many other studies focusing on the effects of *Trichilia catigua* A. Juss on electrophysiological parameters of the heart and on the physiology of membrane channels of cardiomyocytes shall be carried out for elucidating such mechanisms.

What is claimed is:

1. A method for reducing the reoccurrence of ventricular fibrillation, comprising the administration of an alcohol and water extract from plant material of the species *Trichilia catigua* A. Juss to a patient in need thereof.

2. The method of claim 1, comprising reducing the reoccurrence of electrical stimulus-induced ventricular fibrillation.

3. The method of claim 1, comprising post-fibrillation treatment in order to maintain regular cardiac rhythm.

4. A method for reducing the reoccurrence of ventricular fibrillation, wherein said method comprises the administration of a product comprising an alcohol and water extract from plant material of the species *Trichilia catigua* A. Juss to a patient in need thereof.

5. The method of claim 4, comprising reducing the reoccurrence of electrical stimulus-induced ventricular fibrillation.

6. The method of claim 4, comprising post-fibrillation treatment in order to maintain regular cardiac rhythm.

7. The method of claim 1 or claim 4, wherein said extract is administered in association with an extract of *Paullinia cupana* (Sapindaceae), *Croton moritibensis* (Euphorbiaceae) and *Zingiber officinale* (Zingiberaceae).

8. The method of claim 7, wherein said extracts are in the form of a pharmaceutical composition, wherein said pharmaceutical composition comprises a liquid formulation comprising 0.50 to 10.0% m/v of an extract of *Trichilia catigua* A. Juss, 0.10 to 7.50% m/v of an extract of *Paullinia cupana*, 0.01 to 5.50% m/v of an extract of *Croton moritibensis*, 0.10 to 2.00% m/v of an extract of *Zingiber officinale*, and 79.50 to 99.29% m/v of an excipient.

9. The method of claim 7, wherein said extracts are in the form of a pharmaceutical composition, wherein said pharmaceutical composition comprises a liquid formulation comprising 0.50 to 5.00% m/v of an extract of *Trichilia catigua* sp., 0.1 to 5.00% m/v of an extract of *Paullinia cupana*, 0.01 to 5.0% m/v of an extract of *Croton moritibensis*, 0.1 to 0.40% m/v of an extract of *Zingiber officinale*, and 84.60 to 99.24% m/v of an excipient.

10. The method of claim 7, wherein said extracts are in the form of a pharmaceutical composition, wherein said pharmaceutical composition comprises a solid formulation comprising 5 to 100% m/m of an extract of *Trichilia catigua* A. Juss, 2 to 30% m/m of an extract of *Paullinia cupana*, 0.2 to 15.0 m/m of an extract of *Croton moritibensis*, 0.5 to 3.0% m/m of an extract of *Zingiber officinale*, and 2 to 92.30% m/m of an excipient.

11. The method of claim 7, wherein said extracts are in the form of a pharmaceutical composition, wherein said pharmaceutical composition comprises a solid formulation comprising 30 to 50% m/m of an extract of *Trichilia catigua* A. Juss, 10 to 21% m/m of an extract of *Paullinia cupana*, 5 to 12 m/m of an extract of *Croton moritibensis*, 0.5 to 1.5% m/m of an extract of *Zingiber officinale*, and 15.5 to 54.5% m/m of an excipient.

12. The method of claim 7, wherein said extracts are in the form of a pharmaceutical composition, wherein said pharmaceutical composition comprises 17 to 100% m/m of an extract of *Trichilia catigua* A. Juss, 24 to 57% m/m of an extract of *Paullinia cupana*, 17 to 40 m/m of an extract of *Croton moritibensis*, and 2 to 5% m/m of an extract of *Zingiber officinale*.

13. The method of claim 7, wherein said extracts are in the form of a pharmaceutical composition, wherein said pharmaceutical composition comprises 22 to 34% m/m of an extract of *Trichilia catigua* A. Juss, 32 to 48% m/m of an extract of *Paullinia cupana*, 22 to 34 m/m of an extract of *Croton moritibensis*, and 2.5 to 4.0% m/m of an extract of *Zingiber officinale*.

* * * * *